United States Patent
Zhang et al.

(10) Patent No.: US 9,278,994 B2
(45) Date of Patent: Mar. 8, 2016

(54) SHORT ANTIMICROBIAL LIPOPEPTIDES

(71) Applicant: Helix BioMedix Inc., Bothell, WA (US)

(72) Inventors: Lijuan Zhang, Kenmore, WA (US); Robin Carmichael, Redmond, WA (US)

(73) Assignee: HELIX BIOMEDIX, INC, Bothell, WA (US)

( * ) Notice: Subject to any disclaimer, the term of this patent is extended or adjusted under 35 U.S.C. 154(b) by 0 days.

(21) Appl. No.: 14/385,517

(22) PCT Filed: Mar. 7, 2013

(86) PCT No.: PCT/US2013/029696
§ 371 (c)(1),
(2) Date: Sep. 16, 2014

(87) PCT Pub. No.: WO2013/142088
PCT Pub. Date: Sep. 26, 2013

(65) Prior Publication Data
US 2015/0080291 A1    Mar. 19, 2015

Related U.S. Application Data

(60) Provisional application No. 61/613,212, filed on Mar. 20, 2012.

(51) Int. Cl.
| | | |
|---|---|---|
| *A61K 38/05* | (2006.01) | |
| *C07K 5/068* | (2006.01) | |
| *A61K 38/34* | (2006.01) | |
| *A61K 47/48* | (2006.01) | |
| *A61K 38/06* | (2006.01) | |
| *C07K 5/09* | (2006.01) | |

(52) U.S. Cl.
CPC ............. *C07K 5/06086* (2013.01); *A61K 38/05* (2013.01); *A61K 38/06* (2013.01); *A61K 38/34* (2013.01); *A61K 47/48038* (2013.01); *C07K 5/0815* (2013.01)

(58) Field of Classification Search
None
See application file for complete search history.

(56) References Cited

U.S. PATENT DOCUMENTS

| 8,003,608 | B2 | 8/2011 | Luger | |
|---|---|---|---|---|
| 2007/0231284 | A1* | 10/2007 | Pinel et al. | 424/62 |
| 2010/0160213 | A1* | 6/2010 | Shai et al. | 514/9 |

FOREIGN PATENT DOCUMENTS

DE    102004055541 A1    5/2006

OTHER PUBLICATIONS

International Search Report and Written Opinion mailed May 8, 2013. In corresponding application No. PCT/US2013/029696.
International Written Opinion of the International Preliminary Examining Authority mailed Feb. 26, 2014. In corresponding application No. PCT/US2013/029696.
International Preliminary Report on Patentability mailed Jun. 18, 2014. In corresponding application No. PCT/US2013/029696.
Cutuli et al., "Antimicrobial effects of a-MSG peptides," Journal of Leukocyte Biology, vol. 67, Feb. 2000, pp. 233-239.
Mennella et al., "Glycation of lysing-containing dipeptides," http://www.ncbi.nlm.nih.gov/pubmed/16180244, PubMed-NCBI, 2006, 1 Pg.
Hancock et al., "Antimicrobial and host-defense peptides as new anti-infective therapeutic strategies," Nature Biotechnology Review, vol. 24 No. 12, Dec. 2006, pp. 1551-1557.
Hipkiss et al., "Non-enzymatic glycosylation of the dipeptide L-carnosine, a potential anti-protein-cross-linking agent," 1995 Federation of European Biochemical Societies, FEBS Letters 371, pp. 81-85.
Lintner et al., "Biologically active peptides: from a laboratory bench curiosity to a functional skin care product," International Journal of Cosmetic Science, 22, pp. 207-218, (2000).
Makovitzki et al., "Antimicrobial Lipopolypeptides Composed of Palmitoyl Di- and Tricationic Peptides: In Vitro and in Vivo Activities, Self-Assembly to Nanostructures, and a Plausible Mode of Action," Biochemistry, 2008, pp. 10630-10636.
Vogler et al., "Fettsaeurehaltige basische peptide mit antibakterieller wirkung," vol. 47, Fasciculus 2 (1967) No. 61, 19 Pgs.
Kamysz et al., "In Vitro Activities of the Lipopeptides Palmitoyl (Pal)-Lys-Lys-NH2 and Pal-Lys-Lys Alone and in Combination with Antimicrobial Agents against Multiresistant Gram-Positive Cocci," Antimicrobial Agents and Chemotherapy, Jan. 2007, pp. 354-358.

* cited by examiner

*Primary Examiner* — Jeffrey E Russel
(74) *Attorney, Agent, or Firm* — Novak Druce Connolly Bove + Quigg LLP

(57) ABSTRACT

Disclosed are peptides having biological and therapeutic activity. Particularly disclosed are lipidated di- or tri-peptides analogs of KPV or KdPT that exhibit antimicrobial activity. In particular, the peptides of this invention provide enhanced anti-microbial activity over the base tri-peptides, lysine-proline-valine and lysine-d-proline-tyrosine. The disclosed peptides have the general formula of C12-18 lipid-KXZ-NH$_2$i wherein K is lysine; X is proline, d-proline, histidine or arginine; Z is optional and if present Z is valine, threonine, alanine or leucine; and the terminal COOH is NH$_2$ amidated. The C12-18 lipid is preferably the lipid moiety of lauric acid (C12), myristic acid (C14), pentadecanoic acid (C15), palmitic acid (C16), or stearic acid (C18). The invention is further related to methods of using of these peptides to treat various insults, inflammations or bacterial infections affecting the skin and other related mucosal body surfaces such as the oral cavity.

10 Claims, No Drawings

SHORT ANTIMICROBIAL LIPOPEPTIDES

This application is a Section 371, United States national stage filing of PCT/US2013/029696 filed 7 Mar. 2013 which claims benefit of priority to U.S. Provisional Application 61/613,212, filed 20 Mar. 2012, each of which is herein incorporated by reference in its entirety.

FIELD OF THE INVENTION

The invention relates to peptides having biological and therapeutic activity. Particularly, the invention relates to lipidated di- or tri-peptides analogs of KPV or KdPT that exhibit antimicrobial activity. In particular, the peptides of this invention provide enhanced anti-microbial activity over the base tri-peptides, lysine-proline-valine and lysine-d-proline-tyrosine. The invention is further related to methods of using of these peptides to treat various insults, inflammations or bacterial infections affecting the skin and other related body surfaces such as the oral cavity.

BACKGROUND OF THE INVENTION

Researchers have been developing antimicrobial treatments and agents for decades. Recently, there has been a need for new antimicrobial agents for treating an increasing number of drug-resistant bacterial, viral, and fungal infections.

Various bioactive peptides have been reported in both the scientific literature and in issued patents. Peptides historically have been isolated from natural sources, and have recently been the subject of structure-function relationship studies. Additionally, natural peptides have served as starting points for the design of synthetic peptide analogs.

Various patents exist describing cosmetic compositions containing short peptides. For example, U.S. Pat. No. 6,492,326 suggests the preparation and use of skin care compositions containing pentapeptides and skin care active ingredients.

Strom et al. 2003 (*Journal of Medicinal Chemistry* 46: 1567-1570) describe short antibacterial peptides focused mainly on very short peptides (dimers and trimers) containing chemical modifications. Certain hexapeptides are also described. However, there is no testing or discussion of antimicrobial activity of these hexapeptides.

Alpha-melanocyte-stimulating hormone (α-MSH) is a 13-amino acid neuropeptide with potent anti-inflammatory activity. It is produced by posttranslational processing of the larger precursor molecule pre-opiomelanocortin. The carboxy-terminal tripeptide of α-MSH, comprising of residues 11 to 13, KPV, has been demonstrated to exert anti-inflammatory activity in vivo and in vitro (Brzoska, T., Luger, T A. et al., α-melanocyte-stimulating hormone and related tripeptides: biochemistry, anti-inflammatory and protective effects in vitro and in vivo, and future perspectives for the treatment of immune-mediated inflammatory diseases. *Endocrine Reviews* 2009. 29 (5): 581-602). A structurally related derivative, KdPT (KPT) has been described to be collinear to residues 193-195 of IL-1β and seem to be capable of interacting with the IL-1 receptor type I (Luger T. A., and Brzoska T. α-MSH related peptides: a new class of anti-inflammatory and immunomodulating drugs. *Ann Rheum Dis* 2007; 66 (suppl III): iii52-iii55). There was one report suggesting that KPV has antimicrobial influence on *S. aureus* and *C. albicans*, but no MIC was determined (Cutuli M et al., 2000, antimicrobial effects of α-MSH peptides, *J. Leukocyte Biology*, 67:233-239). Unlike KPV, KdPT tripeptide has never been reported to possess antimicrobial influence.

Thus, there is a need to develop peptides having a broad range of potent antimicrobial activity against a number of microorganisms, including gram negative and gram positive bacteria. Cost of manufacture of antimicrobial peptides is also a key consideration to pharmaceutical and cosmetic applications. We disclose in this invention a cost effective short antimicrobial peptides that can be used in pharmaceutical or cosmetic compositions for topical treatment or management of skin conditions associated with bacterial and fungal infections.

SUMMARY OF THE INVENTION

This invention relates to lipidated di- or tri-peptides analogs of KPV or KdPT that exhibit antimicrobial activity. In particular, the peptides of this invention provide enhanced anti-microbial activity over the base tri-peptides, lysine-proline-valine and lysine-dproline-tyrosine. The antibacterial activity targeted by the isolated peptides is directed against those bacteria affecting the skin and associated mucosal surfaces. Though not to be limited to any particular mechanism, the inventive peptides are able to promote skin health by inhibiting bacterial growth and inhibiting associated inflammation from bacterial infection.

One embodiment of the present invention is drawn toward lipidated di- or tri-peptides of the general formula:

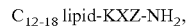

$C_{12-18}$ lipid-KXZ-NH$_2$, wherein K is lysine; X is proline, D-proline (D-isomer of proline), histidine or arginine; Z is optional and if present Z is valine, threonine, alanine or leucine; and the terminal COOH is NH$_2$ amidated. The peptide is lipidated with a $C_{12-18}$ lipid and is preferably the lipid moiety of lauric acid (C12), myristic acid (C14), pentadecanoic acid (C15), palmitic acid (C16), or stearic acid (C18). Pentadecanoyl and palmitoyl are the most preferred lipid groups.

The preferred lipidated di- and tri-amino acids include

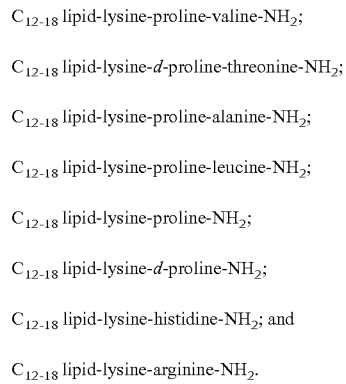

$C_{12-18}$ lipid-lysine-proline-valine-NH$_2$;

$C_{12-18}$ lipid-lysine-*d*-proline-threonine-NH$_2$;

$C_{12-18}$ lipid-lysine-proline-alanine-NH$_2$;

$C_{12-18}$ lipid-lysine-proline-leucine-NH$_2$;

$C_{12-18}$ lipid-lysine-proline-NH$_2$;

$C_{12-18}$ lipid-lysine-*d*-proline-NH$_2$;

$C_{12-18}$ lipid-lysine-histidine-NH$_2$; and $C_{12-18}$ lipid-lysine-arginine-NH$_2$.

Another embodiment of the present invention is drawn toward compositions which contain a pharmaceutically or cosmetically acceptable carrier and one or more of the aforementioned peptides. The peptide in such compositions preferably ranges in concentration from about 0.1 µg/mL to about 20 µg/mL, or from about 0.1 µg/mL to about 10% (w/v). Preferred forms of the composition are aerosols, emulsions, liquids, aqueous solutions, lotions, creams, pastes, ointments, powders and foams, suitable for topical application.

The present invention is also directed towards methods of using the aforementioned compositions for treating or preventing microbial infections of the skin of mammals. Typically, the treatment method entails administering an effective amount of peptide-containing compositions to affected areas of the skin (epidermis) and associated mucosal tissues, for an effective amount of time. The methods may also be useful when the bacterial infection is caused by a bacterium selected from *P. acnes, S. aureus, E. coli* and *C. albicans*.

Additionally, the peptides of the present invention, and compositions containing them, may provide useful features for inclusion in general skin care and cosmetic formulations, such as various skin cosmetics, skin creams, lotions, sunscreens, and therapeutic lotions or creams such as anti-acne formulations.

DETAILED DESCRIPTION OF THE INVENTION

In order that the invention herein described may be more fully understood, the following detailed description is set forth. The invention is generally directed towards compositions and methods comprising antimicrobial lipidated di- or tri-peptides analogs of KPV or KdPT of the general formula:

$C_{12-18}$ lipid-KXZ-$NH_2$, wherein K is lysine; X is proline, d-proline, histidine or arginine; Z is optional and if present Z is valine, threonine, alanine or leucine; and the terminal COOH is $NH_2$ amidated. Examples of saturated or unsaturated fatty acids that can be used to provide the $C_{12-18}$ lipid—component of the compounds of the invention include:

| Systematic name | Common name | Shorthand designation |
|---|---|---|
| dodecanoic acid | lauric acid | 12:0 |
| tetradecanoic acid | myristic acid | 14:0 |
| hexadecanoic acid | palmitic acid | 16:0 |
| heptadecanoic acid | margaric (daturic) acid | 17:0 |
| octadecanoic acid | stearic acid | 18:0 |
| 9-cis-tetradecenoic acid | Myristoleic acid | 14:1 (n-5) |
| 9-cis-hexadecenoic acid | Palmitoleic acid | 16:1 (n-7) |
| 6-cis-hexadecenoic acid | Sapienic acid | 16:1 (n-10) |
| all-cis-7,10,13-hexadecatrienoic acid | | 16:3 (n-3) |
| 9-cis-octadecenoic acid | Oleic acid | 18:1 (n-9) |
| all-cis-9,12-octadecadienoic acid | Linoleic acid | 18:2 (n-6) |

Alpha-melanocyte-stimulating hormone (α-MSH) is a 13-amino acid neuropeptide with potent anti-inflammatory activity. It is produced by posttranslational processing of the larger precursor molecule pre-opiomelanocortin. The carboxy-terminal tripeptide of α-MSH, comprising of residues 11 to 13, KPV, has been demonstrated to exert anti-inflammatory activity in vivo and in vitro (Brzoska, T., Luger, T A. et al., α-melanocyte-stimulating hormone and related tripeptides: biochemistry, anti-inflammatory and protective effects in vitro and in vivo, and future perspectives for the treatment of immune-mediated inflammatory diseases. Endocrine reviews 2009. 29 (5): 581-602). A structurally related derivative, KdPT (KPT) has been described to be collinear to residues 193-195 of IL-1β and seem to be capable of interacting with the IL-1 receptor type I (Luger T. A., and Brzoska T. α-MSH related peptides: a new class of anti-inflammatory and immunomodulating drugs. Ann Rheum Dis 2007; 66 (suppl III): iii52-iii55). There was one report suggesting that KPV has antimicrobial influence on *S. aureus* and *C. albicans*, but no MIC was determined (Cutuli M et al., 2000, antimicrobial effects of α-MSH peptides, J. Leukocyte Biology, 67:233-239). Unlike KPV, KdPT tripeptide has never been reported to possess antimicrobial influence.

We conducted the minimal inhibitory concentration (MIC) determination using CLSI (Clinical and Laboratory standard Institute) recommended standard protocol for antimicrobials (Methods for Dilution Antimicrobial Susceptibility Tests for Bacteria That Grow Aerobically; Approved Standard—Ninth Edition). To our surprise, neither KPV nor KdPT showed detectable MICs at concentrations up to 2000 μg/ml against *E. coli, S. aureus* or yeast. Such poor antimicrobial profile makes both tripeptides far less desirable for therapeutic or cosmetic applications requiring antimicrobial activity.

We modified both peptides via N-terminal acetylation with lipids of various lengths to the alpha amino group of KPV and KdPT. Such modification generates molecules with novel, superior and unexpected antimicrobial activity toward a broad spectrum of microorganisms. The resulting lipotripeptides showed surprisingly superior antimicrobial activity to the parent peptides against Gram-negative and Gram-positive bacteria, and yeast. Lipid length also affects such activity and we found that lipids with carbon number ranging from 12 to 18 were the most effective. After lipidation the MIC was greatly improved in Muller Hinton broth ranging from 1 to 64 μg/ml against *P. acnes, S. aureus, E. coli* and *C. albicans*. Replacing the third residue in Pal-KPV-NH2 with A or L retained antimicrobial activity and this finding promoted us to remove the third amino acid residue from KPV or KdPT. The resulting lipodipeptides, Pal-KP-NH2, Pal-K-dP-NH2, all showed novel antimicrobial activity. In addition, both KP-NH2 and KdP-NH2 showed moderate anti-inflammatory activity against histamine induced IL-6 expression in human skin keratinocytes (data not shown). We further substituted the second residue P or dP with V, A, F, G, S, H, K, I, L, D, R, S, W, or Y. This work provided a group of lipodipeptides with novel antimicrobial activity that has never been reported. The antimicrobial activity can be translated into therapeutic applications in a pharmaceutical or cosmetic preparation.

In summary, the invention is based on the discovery that specific lipodipeptides and lipotripeptides derived from KPV, consisting of lipid-KXZ, where lipid can be selected desirably from Palmitoyl-, Lauroyl-, Myristoyl-, Pentadecanoyl-, and Stearoyl-; and x can be selected from, P, G, I, H, and R, in L- or D-enantiomeric form, Z is optional and if present Z is V, T, A or L, amidated at the carboxy-terminus. Such short lipopeptides are novel antimicrobials against Gram-positive and Gram-negative bacteria including *Escherichia coli* (*E. coli*), *Staphylococcus aureus* (*S. aureus*), *Propionibacterium acnes* (*P. acnes*), dermatophytes such as *Trichophyton* spp., and yeast *Candida* spp., including *C. albicans, C. glabrata* and *C. tropicalis*.

Abbreviations key: Lipids listed above which are coupled via an amide bond to the di- or tri-peptide, using standard peptide chemistry: myr=myristic acid, pen=pentadecanoic acid, pal=palmitic acid, ste=stearic acid, lau=lauric acid. The dextro form of amino acid is abbreviated "d", e.g. dextro form of proline is d-proline. Further, the abbreviations for the amino acids follow conventional usage:

| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |

| | | |
|---|---|---|
| Serine | Ser | S |
| Threonine | Thr | T |
| Tryptophan | Trp | W |
| Tyrosine | Tyr | Y |
| Valine | Val | V |

Details on techniques for formulation and administration of pharmaceuticals may be found in the latest edition of Remington's Pharmaceutical Sciences (Mack Publishing Co, Easton Pa.). Although local topical delivery is desirable, there are other means of delivery, for example: oral, parenteral, aerosol, intramuscular, subcutaneous, transcutaneous, intramedullary, intrathecal, intraventricular, intravenous, intraperitoneal, or intranasal administration. The present invention can be formulated in a number of carrier vehicles, for example, in a spray; an aerosol; a water and an oil-type emulsion; an oil and water-type emulsion; a face cream or body cream; a sun lotion or after-sun lotion; or other topical administration vehicle. Additionally, the peptides of the present invention, and compositions containing them, may provide useful features for inclusion in general skin care and cosmetic formulations, such as various skin cosmetics, skin creams, lotions, sunscreens, and therapeutic lotions or creams such as anti-acne formulations.

As used herein, the term "therapeutic" means an agent utilized to treat, combat, ameliorate, prevent or improve an unwanted condition or disease of a patient. The condition being treated in the present invention includes various bacterial infections that commonly affect the skin or mucosal regions of mammals such as humans. The methods may also be useful when the bacterial infection is caused by a bacterium or fungus selected from *P. acnes, S. aureus, E. coli* and *C. albicans*.

Depending on the specific application contemplated, the pharmaceutical composition provided by the subject invention may be formulated as a solution, suspension, parental preparation, ointment, cream, lotion, spray, powder, or tablet capsule. Parental preparations may include a vehicle such as specially distilled, pyrogen-free water, phosphate buffer, or normal saline. Ointments, creams, lotions and sprays may include a carrier such as vegetable or mineral oil, white petrolatum, or a high molecular weight alcohol, i.e., greater than C.sub.12. Tablets or capsules may include diluents, (e.g., lactose), binders, lubricants (e.g., stearic acid) and a disintegrator (e.g., corn starch).

A mouth spray containing an effective amount of an active agent may also be formulated with one or more lipidated peptides of the present invention. This material may be sprayed as an antimicrobial agent in 0.25 to 0.5 ml. aliquots onto the tooth and gingiva surfaces of each quadrant between 1 and 3 times per day. In the case of denture wearers, the spray may be utilized directly on the denture surface prior to daily insertion of the denture. If desired, a mouthwash formulation may be provided containing an effective amount of the antimicrobial agent.

The compositions of the present invention can also include a pharmaceutically or dermatologically acceptable carrier. Examples of carriers include emulsions and gels. Emulsions are often a mixture of an oil phase and an aqueous phase. The compositions can also comprise exfoliant abrasive materials. The compositions can also comprise a stabilizer. The compositions can also comprise a foam control compound.

The compositions can also include one or more additional skin care active components. Examples of skin care active components include desquamatory actives, anti-acne actives, vitamin B3 compounds, retinoids (including retinol, retinal, retinol esters, retinyl propionate, retinoic acid, and retinyl palmitate), hydroxy acids, radical scavengers, chelators, anti-inflammatory agents, topical anesthetics, tanning actives, skin lightening agents, anti-cellulite agents, flavonoids, antimicrobial actives, skin healing agents, antifungal actives, farnesol, phytantriol, allantoin, salicylic acid, niacinamide, dexpanthenol, tocopherol acetate, and glucosamine.

The compositions can also include sunscreen compounds. Examples of sunscreen compounds include inorganic sunscreen compounds and organic sunscreen compounds. Inorganic sunscreen compounds can include metal oxides such as zinc oxide, titanium oxide, and iron oxide. Organic sunscreen compounds can include octylmethoxycinnamate, octyl salicylate, terephthalylidene dicamphor sulfonic acid, avobenzone, and octocrylene.

Materials and Methods

1. Peptide synthesis. All the disclosed peptides were synthesized using standard Fmoc (9-fluorenylmethoxycarbonyl) solid-phase chemistry. The peptides were prepared as either amidated or free acid sequences using standard amino acids.

2. Bacterial strains and culture conditions. Bacterial strains included in this study are listed in Table 1. *E. coli* UB1005, *S. aureus* SAP0017 (MRSA) and *C. albicans* 105 were grown in Mueller Hinton (MH) (Difco, BD Biosciences, MD) agar plates and broth (2 g of beef extract, 17.5 g of acid hydrolysis of casein and 1.5 g of starch per liter) at 37° C. unless otherwise indicated. Bacteria from frozen stock were subcultured onto freshly made MH agar plates prior to susceptibility testing. For *P. acnes*, the bacterium was grown in BBL™ Brain-Heart infusion (Becton, Dickinson & Company, Sparks Md.) broth or agar plates at 37° C. in anaerobic condition generated using a anaerobic jar and AnaeroGen™ (Oxoid, Basingstoke, Hampshire, England).

3. Determination of antimicrobial activity. The minimal inhibitory concentration (MIC) of each peptide was determined using modified CLSI microtiter broth dilution assay (Methods for Dilution Antimicrobial Susceptibility Tests for Bacteria That Grow Aerobically; Approved Standard—Ninth Edition). An inoculum of $10^5$-$10^6$ colony forming units (CFU)/ml was used or $10^4$ CFU/ml for yeast. The MIC value was taken as the lowest peptide concentration at which more than 90% of microbial growth was inhibited after 15 to 20 h of incubation at 37° C. For *P. acnes*, the incubation was kept under anaerobic condition at 37° C. for 2 weeks before MIC was determined Kill kinetics was performed using a given concentration (about 2-5-fold MIC) of peptide mixed with indicator microorganism. After appropriate dilution the cells were plated on agar plates after defined time intervals and incubated at 37° C. overnight. In the case of *P. acnes* an extended incubation period was required. The CFU was counted and plotted as survival of bacteria after peptide treatment over time, which indicates the effectiveness of a peptide to kill a microbe.

4. Skin tissue toxicity determination. Skin toxicity and compatibility was determined using EpiDerm (EPI-200) skin tissue and MTT Kit (MTT-100) (MatTek, Ashland, Mass.) according to the manufacture's instruction. 1% Triton X-100 and PBS were used as positive (toxic) and negative (non-toxic) control, respectively.

5. Gene profiling analysis. The 84 genes encoding extracellular matrix adhesion molecules in human dermal fibroblasts were analyzed using PCR arrays conducted by Sunny Biodiscovery, Inc (Santa Paula, Calif.). Human dermal fibroblasts were from Zen-Bio, Research Triangle Park, N.C. (cat. #DF-F, lot #DFMF112410). Cells (low passage) were grown in DMEM/10% FCS w/o Phenol Red until they reached the confluent stage afterward they were incubated in duplicates with test materials at 3, 5, or 10 µg/ml or water for 24 h. At the end of the incubation cells were observed under the inverted Nikon TS microscope. None of the experimental conditions were found to be cytotoxic. Qualitative assessment showed more cells undergoing mitosis under test materials at 5 µg/ml than 10 µg/ml, and therefore 5 µg/ml condition was chosen for RNA extraction.

At the end of the incubation period cells were preserved in RNAlater solution (Ambion, Austin, Tex.) for 6 h. RNA was extracted and purified with NucleoSpin RNA II kit from Machery-Nagel, Bethleem, Pa.). Purified total RNA was assessed at 230 nm, 260 nm and 280 nm with Agilent HP-8452A diode array spectrophotometer. The concentration of RNA was equalized across the samples and the expression of genes of interest was measured by real-time quantitative PCR with BioRad iCycler iQ Detection System using PCR arrays PAHS-013A (www.sabiosciences.com/rt_pcr_product/HTML/PAHS-013A.html), with 1st strand synthesis kit, SYBR Green master mix and PCR running conditions from Qiagen (formerly SA Biosciences). Efficiency ΔΔCt method was used for quantification of results, after the normalization of gene expression to 5 housekeeping genes carried with the RT2 Profiler PCR Array Data Analysis version 3.5 software.

Results and Discussion

Both KPV and KdPT tripeptides were known for their anti-inflammatory activities in vitro and in vivo. KPV tripeptide has also been reported to have antimicrobial activity in phosphate buffer against *S. aureus* and *C. albicans* (Cutulis M. et al., Antimicrobial effects of α-MSH peptides. J. Leukocyte Bio. 2000 67:233-239). However the MIC value of KPV has never been determined or reported. Also it is unknown whether KdPT possesses antimicrobial influence or not.

We tested the antimicrobial activity of KPV and K-dPT in culture media using CLSI recommended microbroth dilution assay, a standard assay used for determination of MIC in vitro for antibiotics and antifungals (Methods for Dilution Antimicrobial Susceptibility Tests for Bacteria That Grow Aerobically; Approved Standard—Ninth Edition). To our surprise neither KPV (HB2067, HB2068) nor KdPT (HB2089, HB2090) with or without C-terminal amidation showed detectable MICs at concentrations up to 2000 µg/ml in MH broth (Table 1). This was consistent with the finding described by Rauch and coworkers that KPV failed to inhibit yeast growth at up to 100 µM using a growth assay against *C. albicans* strain SC5314, a standard laboratory strain for antifungal susceptibility experiments (Rauch I., Holzmeister S., and Kofler B. Anti-*Candida* activity of alpha-melanocyte-stimulating hormone (alpha-MSK) peptides. J. Leukoc. Biol. 2009. 85 (3):371-372).

We modified KPV and KdPT with lipids of various lengths aiming to search for analogs with better or improved antimicrobial profile than the parent tripeptides. Acetylation of the tripeptide core revealed surprising results. The lipid length seems to be critical and Table 2 shows the results using KPV as example.

Lipid with carbon number ranging from 11 to 18 appears to positively influence the antimicrobial activity of both KPV and KdPT (Table 1, 2). The optimal lipid length was identified to be of 15 and 16 carbons for KPV and KdPT (Table 1, 2). Such lipids significantly enhance the antimicrobial activity of both peptides towards broad spectrum microorganisms including Gram-positive, Gram-negative bacteria and yeast as evident by SEQ ID NOs, 5 (HB2178), 7 or 24 (HB2180 or HB2200), 17 (HB2192), 23 (HB2199), (Table 1, 2). In fact, the lipopeptides showed nearly 2000-fold improvement in MICs, ranging from 1-64 µg/ml against *P. acnes, S. aureus, E. coli* and *C. albicans*, compared to the parent tripeptide KPV-NH2 or KdPT-NH2 alone that was inactive at up to 2000 ug/ml (Table 1). Increase lipid length to 18-carbon abolishes Gram-negative selective activity but retains both Gram-positive and yeast selective activity (Table 1, 2). We further substituted the third amino acid in Pal-KPV-NH2 with either A or L to obtain SEQ ID NOs 30 (HB2208) and 31 (HB2209). Interestingly, both SEQ ID NOs 30 and 31 maintained decent broad spectrum antimicrobial activity suggesting that the third residue V in Pal-KPV-NH2 may or may not be required for the novel antimicrobial activity observed. In addition to their broad spectrum activity as indicated by the MICs, the analogs including SEQ ID NOs, 5 (HB2178), 7 (2180), (HB2208) and 31 (HB2209) were all cidal and erredicated 5-6 logs of *S. aureus* within 20 min in a kill assay (Table 3). In summary attachment of lipids to KPV-NH2 or KdPT-NH2 with carbon numbers ranging from 12 to 18 allows to generate lipotripeptides with novel broad spectrum antimicrobial activity that has never been reported before. The third residue in Pal-KPV-NH2 or Pal-KdPT-NH2 may or may not be crucial for the observed novel antimicrobial activity. The C-terminal amidation is very critical for the described antimicrobial activity as non-amidated counterparts such as HB2184 and HB2182 were less active or inactive.

That the substitute of the third residue of Pal-KPV-NH2 with A and L did not abolish the activity prompted us to further modifications. We therefore removed the third amino acid residue of both Pal-KPV-NH2 and Pal-KdPT-NH2 to obtain lipodipeptides SEQ ID NO 26 (HB2202) and SEQ ID NO 27 (HB2203). Both derivatives showed novel antimicrobial activity similar to the parent lipotripeptide Pal-KPV-NH2 and Pal-KdPT-NH2 (Table 1). Such activity was unexpected and has never been disclosed. Kill kinetics suggests that both lipodipeptide derivatives were equally cidal and eradicated more than 5 logs of microorganisms including *P. acnes, S. aureus, E. coli* and yeast *C. albicans* within 20 min of direct contact in PBS (Table 3). The antimicrobial activity of the lipodipeptides described in this invention was also evident as both maintained significant killing activity against *S. aureus* in the presence of 10% fetal bovine serum (Table 3). This is particularly of significance. Peptide antibiotics are often a problem due to interference with and binding to host proteins resulting in reduced antimicrobial activity. Considering that skin cuts or lesions including acne lesions often accompany with serum infiltrations on the wounded area, the antimicrobial activity in serum is very important for potential therapeutics.

To make sure Pal-KP-NH2 contains the design for optimal activity, we switched position for P and K to generate HB2251 (Pal-PK-NH2) and HB2255 (Pal-PK-OH). Compare to Pal-KP-NH2, Pal-PK-NH2 showed more than 8-fold reduction in activity. The non-amidated derivatives Pal-PK-OH and Pal-KP-OH were inactive again suggesting the C-terminal amidation being critical for antimicrobial activity.

Potential for dermal irritancy of the lipodipeptides was tested using EpiDerm™ Skin Model (MatTek, Ashland, Mass.) in combination with a modified MTT assay. The EpiDerm™ Skin Model exhibits in vivo-like morphological and growth characteristics which are uniform and highly reproducible. EpiDerm™ consists of organized basal, spinous, granular, and cornified layers analogous to those found in vivo. The tissues were treated with each compound at desired concentration for 20 hr. As seen in Table 1, none of the selected lipopeptides represented by HB2202, HB2203, HB2180, HB2208 and HB2209 exhibited negative effects upon tissue viability at up to 2000 ug/ml.

Encouraged by the novel lipodipeptides HB2202 and HB2203, we extended modifications by substituting the second residue of Pal-KP-NH2 and Pal-K-dP-NH2 with V, A, F, G, L, S, H, K, I, S, R, T, Y, or W. As shown in Table 1, such modification leads to the discovery of a group of extended novel lipodipeptides that exerts either broad spectrum antimicrobial activity (Pal-KH-NH2, Pal-KR-NH2, Pal-KR-OH), or more Gram-positive selective activity (Pal-KG-NH2, Pal-KL-NH2, and Pal-KI-NH2) (Table 1).

Three representative compounds, SEQ ID NO. 26 (HB2202), SEQ ID NO. 41 (HB2242) and SEQ ID NO. 55 (HB2259), were selected for gene profiling study on human dermal fibroblasts. As shown in Table 4, the three compounds showed similar trend/pattern in terms of influence on human dermal fibroblasts. The genes being affected are those that are involved in the wound healing and antifibrosis cascades. The three compounds influence integrins as indicated that HB2202 and HB2242 upregulate ITGA2 (integrin alpha 2) expression while HB2259 induces ITGA6 (integrin alpha 6) (Table 4). The integrins bind to collagens and play important roles in cell to matrix interactions. These proteins are abundantly expressed by basal keratinocytes in intact skin and are required for reepithelialization of human skin wounds. The compounds also modulate the expression of ADAMTS (adam metallopeptidase with thrombospondin type 1) and THBS3 (thrombospondin) (Table 4), both of which are involved in wound healing. In animal model studies down regulation of thrombospondin in THBS-null mice was shown to have enhanced arteriogenesis, angiogenesis and recovery of blood flow following ischemia in comparison to control mice (Kyriakides T R and MacLauchlan S. The role of thrombospondins in wound healing, ischemia, and the foreign body reaction. J Cell Commun Signal 2009. 3:215-225). Also shown in table 4 is that all three compounds significantly down regulate the expression of CTGF (connective tissue growth factor) as well as CTNND1 (catenin). Both CTGF and CTNND1 are associated with fibroproliferative activity, and elevated expression levels have been found in disorders such as keloids and hypertrophic scars (HTS) (Poon R et al., Catenin driven neoplastic and reactive fibroproliferative disorders. PLoS One. 2012; 7:e37940). HTS represents aberrations in the fundamental processes of wound healing, causing excessive collagen production by fibroblasts. Burns, traumatic injuries, and surgical procedures often produce HTS. Wound infection also left the skin with HTS after elimination of the infectious agents such as bacteria and fungi with antimicrobial agents. The lipodipeptides also affect KAL1 (Table 4). This is of particular interesting as it has been found that the protein encoded by the KAL1 gene is involved in modulation of epidermal nerve density in atopic dermatitis. KAL1 overexpression inhibits neurite outgrowth, possibly inhibiting hyperinnervation and abnormal itch perception in atopic dermatitis (Tengara S et al., Keratinocyte-derived anosmin-1, an extracellular glycoprotein encoded by the X-linked Kallmann syndrome gene, is involved in modulation of epidermal nerve density in atopic dermatitis. J Dermatol Sci 2010. 58:64-71). In conclusion, in addition to the discussed broad spectrum antimicrobial activity, the short lipopeptides can activate human dermal cells to promote wound healing and antifibrotic activity. Therefore the lipopeptides are beneficial for wound recovery post antimicrobial treatment.

TABLE 1

Antimicrobial activity and skin tissue toxicity of KPV analogs

| SEQ ID | HB# | Sequence | MIC (µg/ml) | | | | Toxicity EpiDerm[TM] |
|---|---|---|---|---|---|---|---|
| | | | E. coli | S. aureus | C. albicans | P. acnes | |
| 1 | HB2067 | KPV-OH | >2000 | >2000 | >2000 | >2000 | >2000 |
| 2 | HB2068 | KPV-NH2 | >2000 | >2000 | >2000 | >2000 | >2000 |
| 3 | HB2089 | K-dPT-NH2 | >2000 | >2000 | >2000 | >2000 | >2000 |
| 4 | HB2090 | K-dPT-OH | >2000 | >2000 | >2000 | >2000 | >2000 |
| 5 | HB2178 | Pal-K-dPT-NH2 | 64 | 4 | 16 | 2 | >2000 |
| 6 | HB2179 | Dec-K-dPT-NH2 | >2000 | >2000 | >2000 | >2000 | ND |
| 7 | HB2180 | Pal-KPV-NH2 | 128 | 8 | 16 | 1-2 | >2000 |
| 8 | HB2181 | Dec-KPV-NH2 | >2000 | >2000 | >2000 | 1000 | ND |
| 9 | HB2182 | Pal-KdPT-OH | >2000 | >2000 | >2000 | 32 | ND |
| 10 | HB2183 | Dec-KdPT-OH | >2000 | >2000 | >2000 | >2000 | ND |
| 11 | HB2184 | Pal-KPV-OH | >2000 | >2000 | >2000 | 8 | ND |
| 12 | HB2185 | Dec-KPV-OH | >2000 | >2000 | >2000 | >2000 | ND |
| 13 | HB2188 | Octanoyl-KPV-NH2 | >2000 | >2000 | >2000 | >2000 | ND |
| 14 | HB2189 | Undecoyl-KPV-NH2 | 2000 | 1000 | >2000 | 256-500 | ND |
| 15 | HB2190 | Lauroyl-KPV-NH2 | 250 | 250 | >2000 | 64 | ND |
| 16 | HB2191 | Myristoyl-KPV-NH2 | 500 | 250 | 250 | 16 | ND |
| 17 | HB2192 | Pentadecanoyl-KPV-NH2 | 64 | 16 | 32 | 1 | ND |
| 18 | HB2194 | Stearoyl-KPV-NH2 | >2000 | 16 | 16 | 1-2 | ND |
| 19 | HB2195 | Octanoyl-KdPT-NH2 | >2000 | >2000 | >2000 | >2000 | ND |
| 20 | HB2196 | Undecoyl-KdPT-NH2 | 2000 | 1000 | 1000 | 256-500 | ND |
| 21 | HB2197 | Lauroyl-kdPT-NH2 | 1000 | 500 | 500 | 128 | ND |
| 22 | HB2198 | Myristoyl-KdPT-NH2 | 128 | 64 | 64 | 8-16 | ND |
| 23 | HB2199 | Pentadecanoyl-KdPT-NH2 | 64 | 32 | 32 | 2-4 | ND |
| 24 | HB2200 | Pal-K-dPT-NH2 | 64 | 4 | 16 | 2 | ND |
| 25 | HB2201 | Stearoyl-K-dPT-NH2 | 128 | 16 | 8 | 1-2 | ND |
| 26 | HB2202 | Pal-KP-NH2 | 64 | 16 | 16 | 1 | >2000 |
| 27 | HB2203 | Pal-K-dP-NH2 | 128 | 8 | 16 | 1-2 | >2000 |
| 28 | HB2205 | Pal-PV-NH2 | >2000 | >2000 | >2000 | >2000 | ND |
| 29 | HB2207 | Pal-dPS-NH2 | >2000 | >2000 | >2000 | 32 | ND |
| 30 | HB2208 | Pal-KPA-NH2 | 128 | 16 | 16 | 1 | >2000 |
| 31 | HB2209 | Pal-KPL-NH2 | >2000 | 16 | 32 | 4-8 | >2000 |
| 32 | HB2230 | KP-NH2 | >2000 | >2000 | >2000 | >2000 | ND |
| 33 | HB2231 | K-dP-NH2 | >2000 | >2000 | >2000 | >2000 | ND |
| 34 | HB2236 | Pal-KT-NH2 | >2000 | >2000 | >2000 | 256-1000 | ND |
| 35 | HB2237 | Pal-K-dT-NH2 | >2000 | >2000 | >2000 | 128-256 | ND |

TABLE 1-continued

Antimicrobial activity and skin tissue toxicity of KPV analogs

| SEQ ID | HB# | Sequence | MIC (µg/ml) E. coli | MIC (µg/ml) S. aureus | MIC (µg/ml) C. albicans | MIC (µg/ml) P. acnes | Toxicity EpiDerm™ |
|---|---|---|---|---|---|---|---|
| 36 | HB2238 | Pal-KK-NH2 | 2 | 4 | 16 | ND | ND |
| 37 | HB2239 | Pal-KV-NH2 | >2000 | >2000 | >2000 | >2000 | ND |
| 38 | HB2240 | Pal-KA-NH2 | >2000 | >2000 | >2000 | >2000 | ND |
| 40 | HB2241 | Pal-KF-NH2 | >2000 | >2000 | >2000 | >2000 | ND |
| 41 | HB2242 | Pal-KH-NH2 | 16 | 4 | 16 | 1-2 | ND |
| 42 | HB2243 | Pal-KG-NH2 | >2000 | 250 | >2000 | 32-64 | ND |
| 43 | HB2244 | Pal-KL-NH2 | >2000 | 250 | >2000 | 8 | ND |
| 44 | HB2245 | Pal-KS-NH2 | >2000 | 1000 | >2000 | 128 | ND |
| 45 | HB2246 | Pal-KI-NH2 | >2000 | 128 | >2000 | >2000 | ND |
| 46 | HB2247 | Pal-KY-NH2 | >2000 | >2000 | >2000 | >2000 | ND |
| 47 | HB2248 | Pal-KW-NH2 | >2000 | >2000 | >2000 | >2000 | ND |
| 48 | HB2251 | Pal-PK-NH2 | 2000 | 128 | 128 | 4-16 | ND |
| 49 | HB2252 | Pal-KD-NH2 | >2000 | >2000 | >2000 | ND | ND |
| 50 | HB2253 | Pal-KR-OH | 500 | 16 | 32 | 2-4 | ND |
| 51 | HB2255 | Pal-PK-OH | >2000 | >2000 | >2000 | >2000 | ND |
| 52 | HB2256 | Pal-K-dP-OH | >2000 | >2000 | >2000 | >2000 | ND |
| 53 | HB2257 | Pal-KP-OH | >2000 | >2000 | >2000 | >2000 | ND |
| 54 | HB2258 | Pal-KK-OH | 32 | 16 | 64 | 1-4 | ND |
| 55 | HB2259 | Pal-KR-NH2 | 8 | 2 | 16 | <1 | ND |

TABLE 2

Effect of Lipid length on the antimicrobial activity of KPV-NH2

| SEQ ID | HB# | Sequence | Lipid length | MIC (µg/ml) E. coli | MIC (µg/ml) S. aureus | MIC (µg/ml) C. albicans |
|---|---|---|---|---|---|---|
| 13 | HB2188 | Octanoyl-KPV-NH2 | 8C | >2000 | >2000 | >2000 |
| 8 | HB2181 | Dec-KPV-NH2 | 10C | >2000 | >2000 | >2000 |
| 14 | HB2189 | Undecoyl-KPV-NH2 | 11C | 2000 | 1000 | >2000 |
| 15 | HB2190 | Lauroyl-KPV-NH2 | 12C | 250 | 250 | >2000 |
| 16 | HB2191 | Myristoyl-KPV-NH2 | 14C | 500 | 250 | 250 |
| 17 | HB2192 | Pentadecanoyl-KPV-NH2 | 15C | 64 | 16 | 32 |
| 5 | HB2178 | Palmitoyl-KPV-NH2 | 16C | 128 | 8 | 16 |
| 18 | HB2194 | Stearoyl-KPV-NH2 | 18C | >2000 | 16 | 16 |

TABLE 3

Kill kinetics of selected KPV analogs
Kill kinetics shown as survival of microbes
over time (CFU/ml) (detection limit 10 CFU/ml)

S. aureus SAP0017 (MRSA) in PBS

| SEQ ID | HB# | 0 hr | 20 min | 1 hr | 2 hr | 3 hr |
|---|---|---|---|---|---|---|
| — | PBS | 23050000 | 23050000 | 23050000 | 23050000 | 23050000 |
| 2 | HB2068 | 23050000 | 23050000 | 23050000 | 23050000 | 23050000 |
| 3 | HB2089 | 23050000 | 23050000 | 23050000 | 23050000 | 23050000 |
| 5 | HB2178 | 23050000 | <10 | <10 | <10 | <10 |
| 7 | HB2180 | 23050000 | <10 | <10 | <10 | <10 |
| 26 | HB2202 | 23050000 | <10 | <10 | <10 | <10 |
| 27 | HB2203 | 23050000 | <10 | <10 | <10 | <10 |
| 30 | HB2208 | 23050000 | <10 | <10 | <10 | <10 |
| 31 | HB2209 | 23050000 | <10 | <10 | <10 | <10 |

P. acnes ATCC11827 in PBS

| SEQ ID | HB# | 0 hr | 20 min | 1 hr | 2 hr | 3 hr |
|---|---|---|---|---|---|---|
| — | PBS | 750000 | 750000 | 750000 | 750000 | 750000 |
| 2 | HB2068 | 750000 | 750000 | 750000 | 750000 | 750000 |
| 3 | HB2089 | 750000 | 750000 | 750000 | 750000 | 750000 |
| 5 | HB2178 | 750000 | 20 | <10 | <10 | <10 |
| 7 | HB2180 | 750000 | <10 | <10 | <10 | <10 |
| 26 | HB2202 | 750000 | <10 | <10 | <10 | <10 |
| 27 | HB2203 | 750000 | <10 | <10 | <10 | <10 |

TABLE 3-continued

Kill kinetics of selected KPV analogs
Kill kinetics shown as survival of microbes
over time (CFU/ml) (detection limit 10 CFU/ml)

| | | | | | | |
|---|---|---|---|---|---|---|
| 30 | HB2208 | 750000 | <10 | <10 | <10 | <10 |
| 31 | HB2209 | 750000 | <10 | <10 | <10 | <10 |

*C. albicans* 105 in PBS

| SEQ ID | HB# | 0 hr | 20 min | 1 hr | 2 hr | 3 hr |
|---|---|---|---|---|---|---|
| — | PBS | 1300000 | 1300000 | 1300000 | 1300000 | 1300000 |
| 2 | HB2068 | 1300000 | 1300000 | 1300000 | 1300000 | 1300000 |
| 3 | HB2089 | 1300000 | 1300000 | 1300000 | 1300000 | 1300000 |
| 26 | HB2202 | 1300000 | 3000 | 150 | <10 | <10 |
| 27 | HB2203 | 1300000 | 2980 | 160 | 30 | <10 |

*S. aureus* SAP0017 (MRSA) in 10% fetal bovine serum

| SEQ ID | HB# | 0 hr | 2 hr | 3 hr | 5 hr | 6 hr |
|---|---|---|---|---|---|---|
| — | 10% serum in PBS | 30900000 | 30900000 | 30900000 | 30900000 | 30900000 |
| 2 | HB2068 | 30900000 | 30900000 | 30900000 | 30900000 | 30900000 |
| 3 | HB2089 | 30900000 | 30900000 | 30900000 | 30900000 | 30900000 |
| 26 | HB2202 | 30900000 | 4850 | 1250 | 110 | 50 |
| 27 | HB2203 | 30900000 | 1927000 | 142500 | 68560 | 34280 |

TABLE 4

Gene profiling study on human dermal fibroblasts

| | | Fold change (peptide vs. PBS control) Up (+) or down (−) regulation | | |
|---|---|---|---|---|
| Symbol | Name of gene | HB2202 | HB2242 | HB2259 |
| ADAMTS | Adam metallopeptidase with thrombospondin type I | 3.8106 | 4.7899 | 2.4284 |
| CDH1 | Cadherin type I, E-cadherin | 1.3566 | 1.9725 | 1.0718 |
| COL1A1 | Collagen type 1 alpha 1 | −1.0867 | 1.1975 | −1.8661 |
| COL8A1 | Collagen type VIII alpha-1 | 1.4948 | −1.4044 | −2.5847 |
| CTGF | Connective tisue growth factor | −2.9485 | −1.8921 | −3.0314 |
| CTNND1 | Catenin (cadherin-associated protein), delta 1 | −2.395 | −2.0279 | −1.1487 |
| HAS1 | Hyaluronan synthase 1 | −2.395 | −2.3295 | −3.0314 |
| ITGA2 | Integrin alpha 2 | 2.2038 | 2.114 | 1.3195 |
| ITGA6 | Integrin alpha 6 | 1.2658 | −1.014 | 2.1435 |
| ITGA7 | Integrin alpha 7 | −1.815 | −2.0279 | −1.8661 |
| ITGB2 | Integrin beta 2 | 2.2038 | 1.3947 | 2.1435 |
| KAL1 | Kallmann syndrome 1 sequence | 3.5801 | 1.8404 | 1.2311 |
| MMP1 | Matrix metallopeptidase 1 | 2.362 | 1.7171 | 1.1487 |
| MMP8 | Matrix metallopeptidase 8 | 2.362 | −1.6472 | 2.1435 |
| MMP9 | Matrix metallopeptidase 9 | −1.2834 | −1.6472 | −2.1435 |
| MMP10 | Matrix metallopeptidase 10 | 2.9079 | 1.2142 | 1.6245 |
| MMP13 | Matrix metallopeptidase 13 | 1.0281 | −2.4967 | −3.249 |
| MMP14 | Matrix metallopeptidase 14 | −1.0425 | 1.2142 | −2.4623 |
| SELE | E-selectin | 2.0562 | 1.3947 | 1.0718 |
| THBS3 | Thrombospondin | −1.9453 | −3.0738 | −1.6245 |

The following examples are included to demonstrate certain preferred embodiments of the invention.

Wound infection is a significant problem which is exacerbated by the increasing frequency of multi-drug resistant pathogens like MRSA. The current invention can be applied, therapeutically or cosmetically, to treat, improve and prevention of skin conditions associated to bacteria including acne, atopic dermatitis, rosacea, or fungi including dandruff and athlete foot.

*S. aureus* is a major cause of hospital-acquired infections, most frequently associated with the bloodstream, skin and soft tissue, ventilator-assisted pneumonia and catheters. The increasing frequency of infections caused by methicillin-resistant *S. aureus* (MRSA) is of particular concern, especially in the United States where the prevalence is more than 55% in the intensive care unit and the incidence causes longer hospital stays, higher costs and higher risk of death. Community-acquired MRSA (CA-MRSA), genotypically distinct from HA-MRSA, has also now become an established threat among patients without traditional risk factors. In addition to *S. aureus*, the Gram-positive bacteria *Streptococcus pyogenes* is a major cause of complicated skin and skin structure infections (SSTI). The current invention provides a potential prevention and treatment against MRSA associated infections.

Acne vulgaris is a common human skin disease, characterized by areas of skin with seborrhea, comedones, papules, pustules, nodules and possibly scarring. The areas affected by acne include the face, the upper part of the chest, and the back. Severe acne is inflammatory, but acne can also manifest in noninflammatory forms. The bacterium, *Propionibacterium acnes*, can cause inflammation, leading to inflammatory lesions in the dermis around the microcomedo or comedone, which results in redness and may result in scarring or hyperpigmentation. The antimicrobial short lipopeptides could be used for blemish control in the form of, but not limited to, a pen, foam, wipes, creams, lotions, sprays, toners and/or cleansers. Another potential use would be to use the current art in combination with, but not limited to, salicylic acid or retinoids.

Folliculitis is the word used to describe any inflammation of one or more hair follicles anywhere in the skin including pseudofolliculitis barbae such as razor bumps and scalp folliculitis especially prominent in African American men. Folliculitis is an infection of the hair follicles. Mild cases tend to cause itching while severe cases can lead to deep scarring. It is caused by bacteria that enter the skin through the small opening of the hair follicle. In most cases of folliculitis, the damaged follicles are then infected with the bacteria *Staphylococcus*. Barber's itch is a *staph* infection of the hair follicles in the beard area of the face, usually the upper lip. Tinea barbae is similar to barber's itch, but the infection is caused by a fungus. There are tips that may help to prevent this skin condition, such as using an anti-bacterial soap and scalp folliculitis shampoo. Also hydrocortisone, antibiotic, or tretinoin cream has been used to treat razor bumps caused irritation and pimples. The broad spectrum antimicrobial lipopeptides described in this invention should be ideal for disorder caused by damage to the follicles, by a blocked follicle, by shaving, or by friction caused by clothing, helmet straps, and the like, in the neck, groin, or genital area.

Dandruff is a common chronic scalp condition marked by itching and flaking of the skin on the scalp. *Malassezia* species are well known yeasts that cause of common skin diseases including dandruff, pityriasis versicolor, seborrheic dermatitis, psoriasis, and atopic dermatitis in humans. Tinea capitis, also known as ringworm of the hair or ringworm of the scalp, is a superficial fungal infection of the scalp. The disease is primarily caused by dermatophytes in the *Trichophyton* and *Microsporum* genera that invade the hair shaft. Cases of *Trichophyton* infection predominate from Central America to the United States and in parts of Western Europe. The disease is infectious and can be transmitted by humans, animals or objects that harbor the fungus. Carrier states also exist where the fungus is present on the scalp but no clinical signs or symptoms. Athlete foot also known as ringworm of the foot or tinea pedis, is also a fungal infection of the skin of the feet that causes scaling, flaking, and itch of the effected areas. It is caused by the *Trichophyton* spp. In some cases, secondary bacterial infection can accompany the fungal infection. Antifungals such as terbinafine, itraconazole and fluconazole have started to gain acceptance for treatment. The lipodipeptides with broad spectrum activity against bacteria and fungi disclosed herein could be of potential as topical treatment for prevention and resolve of the conditions described.

Atopic dermatitis (AD) is an inflammatory, chronically relapsing, non-contagious and pruritic skin disorder, affecting 15-30% of children and 2-10% of adults. Sometimes called eczema or atopic eczema, atopic dermatitis is most common in babies and children. it is characterized by pruritus, eczematous lesions, xerosis (dry skin), and lichenification (thickening of the skin and an increase in skin markings). The most common bacteria found on AD skin is *S. aureus*. In fact, more than 90% of AD patients are colonized with *S. aureus* on lesional and non-lesional skin vs. 5% on healthy skin. AD skin showed defective epidermal barrier function as well as deficiency in the innate immune system of the epidermis as suggested by decrease expression of antimicrobial peptides. The lipopeptides described here with antimicrobial activity plus antiinflammatory should be an alternative for AD care.

Halitosis, also known as bad breath, is a term used to describe noticeably unpleasant odors exhaled in breathing. Halitosis is estimated to be the third most frequent reason for seeking dental aid, following tooth decay and periodontal disease. Bad breath and gum disease are caused by gram-negative bacteria such as *Porphyromonas gingivalis, Actinobacillus actinomycetemcomitans, Bacteroides* spp. The bacteria also cause severe inflammation of the epithelial lining of the oral cavity. Anti-Gram-negative selective peptides with antinflammatory activity would be ideal to maintain a healthy oral care.

Triclosan is a chlorinated aromatic compound with antibacterial, antifungal and antiviral properties. It is used in a variety of common household products, including soaps, mouthwashes, dish detergents, toothpastes, deodorants, and hand sanitizers. Reports have suggested that triclosan can combine with chlorine in tap water to form chloroform, which the United States Environmental Protection Agency classifies as a probable human carcinogen, meaning it likely causes cancer. The antimicrobial lipodipeptides disclosed herein have great potential in replacing triclosan for the right antibacterial and antifungal properties without carcinogenic risk.

Likewise, body odor is also influenced by the actions of the members of *Corynebacterium*. The antimicrobial property of the described art can be incorporated into cosmetic powders, gels, semi-solids, creams or other forms as underarm or foot deodorants.

Bacterial vaginosis (BV) is the most general cause of vaginal infection known as vaginitis. Normally it is not considered to be a 'sexually transmitted infection'. Bacterial vaginosis is affecting 20% to 70% of women. The strong odor and abnormal vaginal discharge are the most common symptoms of the disease besides itching and burning sensations. Vaginal candidiasis is an infection of the vagina involving overgrowth of a yeast, or fungus, known as *Candida*. This yeast is normally present in the mouth, gut and vagina, as are a number of other organisms. If the balance of microorganisms is disrupted, as can occur with taking broad spectrum antibiotics, hormonal fluctuations, and other conditions, an overgrowth of yeast can occur. Vaginal candidiasis, often referred to as a "yeast infection," is a common problem, affecting nearly 75% of adult women in their lifetime. Also associated with vaginal inflammation are the non-albican *Candida* spp such as *C. glabrata* and *C. tropicalis*; Herpes and Group B *Streptococcus*. The conditions varies and can be worsened due to the loss of *Lactobacillus* spp, a natural commensal that functions as a protective barrier against opportunistic pathogens. Therefore using antimicrobial peptides disclosed herein to control the indicative microbes in but not limited to lubricants, for example, might provide effective care as feminine hygiene products.

Cosmetics manufacturers add chemical preservatives to makeup and lotions to kill bacteria and extend the shelf life of these products. However, some preservatives cause rashes and other allergic reactions, and studies have linked some of these agents to cancer and other health problems. Synthetic paraben preservatives such as methylparaben, butylparaben and ethylparaben are found in more than 70 percent of cosmetics, skin lotions and deodorants. Paraben preservatives replicate the effects of estrogen. Even small amounts of these potent chemicals can knock your body's natural hormonal system out of balance. Artificially-triggered estrogen imbalances have been linked to breast cancer in women and testosterone deficiencies in young boys. The cosmetics industry also uses formaldehyde as a preservative. Even though the amount added to makeup is small, it can cause an allergic reaction in those who are sensitive to the chemical. Therefore, one of the potential applications of the broad spectrum of antimicrobial lipodipepitdes described, being cost effective, could be to replace the harmful chemicals as preservatives for the cosmetic industry.

The compositions used to deliver the peptides in the above therapeutic method can be an aerosol, emulsion, liquid, lotion, cream, paste, ointment, powder, or foam, or other pharmaceutically acceptable formulation. Furthermore, the peptides can be delivered using less involved formulations such as deionized/distilled water, PBS or standard medical saline solutions. Generally, a pharmaceutically acceptable formulation would include any carrier suitable for use on human skin. Such pharmaceutically acceptable carriers include ethanol, dimethyl sulfoxide, glycerol, silica, alumina, starch, and equivalent carriers and diluents. The formulation may optionally have cosmetic appeal, and/or contain other agents such as retinoids or other peptides that can act as adjuvants for the therapeutic action of the inventive peptides.

Antibiotics can also be added to the formulation in order to ward off infection, thereby permitting maximal healing processes to occur. The concentration of the peptide in the composition can be about 0.1 µg/mL to about 50 µg/mL or about 0.1 µg/mL to about 10% (w/v); however, the ultimate concentration employed may vary outside these ranges, depending on the nature of the wound/tissue condition, the bioactivity of the inventive peptide and the use of any adjuvant or technique to obtain enhanced composition absorption.

The compositions of the present invention can contain one or more additional agents that exert skin care activity.

In a preferred embodiment of the instant invention, where the composition is to be in contact with human keratinous tissue, any additional components besides the inventive peptides should be suitable for application to keratinous tissue; that is, when incorporated into the composition, such other components demonstrate undue toxicity, incompatibility, instability, allergic response, and the like within the scope of sound medical judgment. The CTFA Cosmetic Ingredient Handbook, Second Edition (1992) describes a wide variety of non-limiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g. clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, cosmetic biocides, denaturants, drug astringents, external analgesics, film formers or materials, opacifying agents, pH adjusters, propellants, reducing agents, sequestrants, skin bleaching and lightening agents (e.g. hydroquinone, kojic acid, ascorbic acid, magnesium ascorbyl phosphate, ascorbyl glucosamine), skin-conditioning agents (e.g. humectants), skin soothing and/or healing agents (e.g. panthenol and its derivatives, aloe vera, pantothenic acid and its derivatives, allantoin, bisabolol, and dipotassium glycyrrhizinate), skin treating agents, thickeners, and vitamins and derivatives thereof.

The administration of the inventive peptides and associated compositions may be made to humans and animals, including all mammals. Application may also be made in combination with typical and/or experimental materials such as tissue grafts, tissue culture products, oxygen and dressings.

List of Commonly Used Dressings

| Categories of Wound Dressings | Products |
|---|---|
| Films | Bioclusive ™ (Johnson & Johnson Medical, Inc) |
| | Omiderm ™ (omicron Scientific Ltd.), |
| | Opsite* (Smith & Nephew United, Inc) |
| | Polyskin ®II transparent dressing (Kendall Healthcare) |
| | Tegaderm ™ (3M Health Care) |
| Hydrogels | Intrasite ™ (Smith & Nephew United, Inc), |
| | Nu-Gel ™ (Johnson &Johnson Medical, Inc.) |
| | Vigilon ® (Bard Medical Division) |
| Hydrocolloids | Comfeel ® (Coloplast Sween Corp.) |
| | DuoDerm ® (ConvaTec ®) |
| | Restore ™ (Hollister Incorporated) |
| Polysaccharides | Bard Absorption Dressing* (Bard Medical Division) |
| | Debrisan (Johnson & Johnson Medical, Inc.) |
| | DuoDerm ® Granules (ConvaTec ®) |

-continued

| Categories of Wound Dressings | Products |
|---|---|
| Alginates | Kaltostat ® (ConvaTec ®) |
| | Sorbsan ™ (Dow Hicham Pharmaceuticals Inc) |
| Foam Dressings | Allevyn* (Smith & Nephew United, Inc) |
| | Lyofoam ® (Acme United Corporation) |
| Laminates | Biobrane ® (Dow Hickam Pharmaceuticals Inc) |

*Atsterisks refer to individual company trademarks

In general, the composition can be administered topically, orally, transdermally, systemically, or by any other method known to those of skill in the art to be useful to deliver the inventive peptides to the injury site. Compositions may also be applied in an in vitro or ex vivo manner, either to cells or patient grafts growing in culture, for example.

Due to their small size, the peptides are expected to be able to gain by themselves some level of permeability through the skin; however, certain techniques may be used to amplify this movement. For example, lipophilic (non-polar) groups can be added to the peptides, or the peptides can be delivered to the skin in a lipophilic excipient, in order to enhance peptide accessibility to the stratum corneum to allow translocation to the lower epidermal layers. In this manner such lipophilic modifications may be considered as a pro-drug. Permeation enhancers such as known solvents and surfactants may be used in the excipient to allow better peptide absorption. Special techniques that are anticipated to be useful in enhancing peptide access to the targeted tissue/injury include iontophoresis, electrophoresis and ultrasound. An iontophoretic device consists of two electrodes immersed in an electrolyte solution and placed on the skin. When an electric current is applied across the electrodes, an electric field is created across the stratum corneum that drives the delivery of the peptides. Electroporation involves the application of high-voltage electric pulses to increase the permeation through lipid bilayers. This differs from iontophoresis in the duration and intensity of the application of electrical current (iontophoresis uses a relatively constant low-voltage electric field). The high-voltage electric pulse of electroporation is believed to induce a reversible formation of hydrophilic pores in the lipid lamellae membranes that can provide a high degree of permeation enhancement. Ultrasound applies sound waves having a frequency greater than 16 kHz to the skin, which causes compression and expansion of the tissue through which the sound waves travel. The resulting pressure variations cause a number of processes (e.g., cavitation, mixing, increase in temperature) that may enhance permeation of the peptides.

All the above peptide formulations and uses are well known in the art. Additional modes of preparing and using the inventive peptides are described, for example, in U.S. Pat. Nos. 6,492,326 and 6,974,799, both of which are incorporated herein by reference in their entirety.

All of the compositions or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope of the invention.

What is claimed is:

1. A method for treating a microbial infection of the skin or mucosal tissue of a mammal, the method comprising administering to the infected area of said mammal a therapeutically effective amount of a composition comprising at least one peptide of the formula $C_{12-18}$ lipid-lysine-proline-$NH_2$ or $C_{12-18}$ lipid-lysine-$d$-proline-$NH_2$, and a pharmaceutically acceptable carrier for an effective amount of time.

2. The method of claim 1, wherein the therapeutically effective amount of the composition comprises the peptide at a concentration ranging from about 0.1 μg/mL to about 10% (w/v).

3. The method of claim 1, wherein the microbial infection is caused by a microbe selected from the group consisting of *P. acnes, S. aureus, E. coli* and *C. albicans*.

4. The method of claim 1, wherein the peptide of the composition is palmitoyl-lysine-proline-$NH_2$;
palmitoyl-lysine-d-proline-$NH_2$;
myristoyl-lysine-d-proline-$NH_2$; or
pentadecanoyl-lysine-d-proline-$NH_2$.

5. The method of claim 1 where the microbial infection of the skin is acne, atopic dermatitis, rosacea, bacterial vaginosis, dandruff or athlete's foot.

6. A method for healing a wound in a mammal comprising applying to wounded skin tissue a therapeutically effective amount of a composition comprising at least one peptide of the formula:

$C_{12-18}$ lipid-lysine-proline-$NH_2$;

$C_{12-18}$ lipid-lysine-histidine-$NH_2$; or $C_{12-18}$ lipid-lysine-arginine-$NH_2$;

and a pharmaceutically carrier.

7. The method of claim 6, wherein the wounded skin tissue is hypertrophic scarring, rosacea, or eczematous lesions.

8. The method of claim 7 wherein the hypertrophic scarring is caused by acne, folliculitis, burn wounds, traumatic injuries, surgical procedures or skin infection due to microbes.

9. The method of claim 6 where the peptide is palmitoyl-lysine-proline-$NH_2$;
palmitoyl-lysine-histidine-$NH_2$; or
palmitoyl-lysine-arginine-$NH_2$.

10. The method of claim 1 wherein the microbial infection is a cause of body odor, halitosis or gum disease.

* * * * *